United States Patent

Herbst et al.

[11] Patent Number: 5,872,139
[45] Date of Patent: Feb. 16, 1999

[54] HETEROCYCLYMETHYLAMINO DERIVATIVES OF CYCLOBUTENE-3,4-DIONES

[75] Inventors: David R. Herbst, Wayne, Pa.; John A. Butera, Clarksburg; Russell F. Graceffa, Plainsboro, both of N.J.

[73] Assignee: American Home Products Corporation, Madison, N.J.

[21] Appl. No.: 873,132

[22] Filed: Jun. 10, 1997

Related U.S. Application Data

[60] Provisional application No. 60/019,977 Jun. 17, 1996.
[51] Int. Cl.[6] .......................... A61K 31/34; A61K 31/44; C07D 307/81; C07D 213/50
[52] U.S. Cl. ......................... 514/357; 514/256; 514/469; 546/334; 544/335; 549/467
[58] Field of Search ............................ 546/334; 549/467; 544/335; 514/357, 256, 469

[56] References Cited

U.S. PATENT DOCUMENTS

| | | | |
|---|---|---|---|
| 4,390,701 | 6/1983 | Algieri et al. | 546/235 |
| 4,673,747 | 6/1987 | Nobara et al. | 546/334 |
| 5,354,746 | 10/1994 | Chandrakumar et al. | 514/211 |
| 5,397,790 | 3/1995 | Butera et al. | 514/310 |
| 5,401,753 | 3/1995 | Butera et al. | 514/311 |
| 5,403,853 | 4/1995 | Butera et al. | 514/399 |
| 5,403,854 | 4/1995 | Butera et al. | 514/415 |
| 5,464,867 | 11/1995 | Antane et al. | 514/524 |
| 5,466,712 | 11/1995 | Butera et al. | 514/524 |

FOREIGN PATENT DOCUMENTS

| | | |
|---|---|---|
| 112142 | 12/1983 | European Pat. Off. . |
| 112704 | 12/1983 | European Pat. Off. . |
| 177016 | 10/1985 | European Pat. Off. . |
| 426379 | 10/1990 | European Pat. Off. . |

OTHER PUBLICATIONS

Tietze et al., Chem. Berg., 1991, 124, 1215–1221.
Tietze et al., Bioconjugate Chem., 1991, 2, 148–153.
Ehrhardt et al., Chem. Ber., 1977, 110, 2506–2523.
Neuse et al., Liebigs Ann. Chem., 1973, 619–632.
Takeno et al. Public Patent Disclosure Bull. No. 6–92915 (Japan), (1994).

*Primary Examiner*—Bernard Dentz
*Attorney, Agent, or Firm*—Rebecca R. Barrett

[57] ABSTRACT

The compounds of the formula:

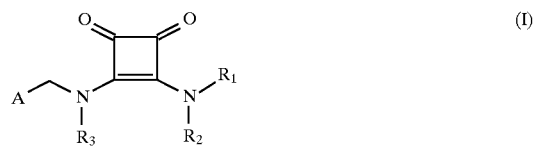

wherein $R_1$ and $R_2$ are, independently, hydrogen, straight chain alkyl, branched chain alkyl, cycloalkyl, bicycloalkyl or aralkyl, wherein the aromatic moiety of the aralkyl group may be optionally substituted with one to three straight chain alkyl, halogen, nitro, cyano, alkoxy, alkoxycarbonyl, trifluoromethyl or trifluoromethoxy groups; $R_3$ is hydrogen, formyl, alkanoyl, alkenoyl, alkylsulfonyl, aroyl, arylalkenoyl, arylsulfonyl, arylalkanoyl or arylalkylsulfonyl; A is selected from the group consisting of:

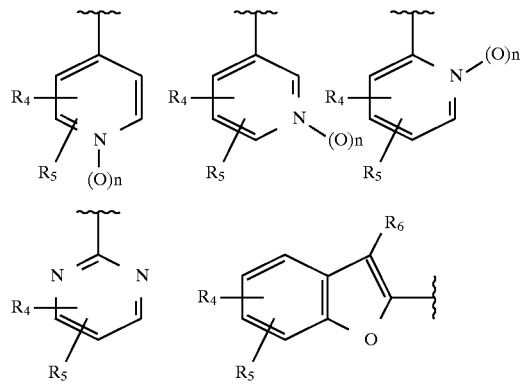

wherein n is 0 or 1; $R_4$, $R_5$ and $R_6$ are, independently, cyano, nitro, amino, alkyl, perfluoroalkyl, alkoxy, perfluoroalkoxy, alkylamino, dialkylamino, sulfamyl, alkylsulfonamido, arylsulfonamido, alkylcarboxamido, arylcarboxamido, alkanoyl, alkylsulfonyl, perfluoroalkylsulfonyl, arylsulfonyl, chloro, bromo, fluoro, iodo, 1-imidazolyl, carboxyl or hydrogen; or a pharmaceutically acceptable salt thereof, relax smooth muscles.

22 Claims, No Drawings

HETEROCYCLYMETHYLAMINO DERIVATIVES OF CYCLOBUTENE-3,4-DIONES

BACKGROUND OF INVENTION

This application claims the benefit of U.S. Provisional Application No. 60/019,977 filed Jun. 17, 1996.

The present invention relates to novel heterocyclylmethyl amino derivatives of cyclobutene 3-4-diones having pharmacological activity, to a process for their preparation, to pharmaceutical compositions containing them and to their use in the treatment of disorders associated with smooth muscle contraction via potassium channel modulation. Such disorders include, but are not limited to: urinary incontinence, asthma, premature labor, irritable bowel syndrome, congestive heart failure, angina, cerebral vascular disease and hypertension.

Stemp et al. (EP-426379) disclose a class of amino substituted cyclobutenedione derivatives of chromans described as having blood pressure lowering activity and bronchodilatory activity. Takeno et al. report a series of diaminocyclobuten-3,4-diones in Public Patent Disclosure Bulletin No. 6-92915. Our own efforts in this area have been disclosed in the following U.S. Pat. Nos. 5,464,867; 5,466,712; 5,403,853; 5,403,854; 5,397,790 and 5,401,753. Several series of 1-amino-2-phenylalkylamino-cyclobutene-3,4-diones are reported as H-2 receptor antagonists by Algieri et al. in U.S. Pat. No. 4,390,701. Several related 1-amino-2-phenoxyalkylamino derivatives are disclosed by Nohara et al. in U.S. Pat. No. 4,673,747. Additionally, several related 1-amino-2-pyridyloxyalkylamino derivatives are disclosed by Nohara et al. in EP-177016. The compounds of Nohara et al. are reported as H-2 receptor antagonists.

A 4-pyridinylmethylamino derivative of cyclobutendione was disclosed by Chandrakumar et al. in U.S. Pat. No. 5,354,746 to possess analgesic activity. The compounds of the Chandrakumar series require the presence of a tricyclic dibenzoxazepine moiety. A 3-pyridinylmethylamino derivative of cyclobutendione was disclosed by Ife in EP-112704 and was reported to be an H-2 antagonist. The compounds of the Ife series require the presence of an N'-pyridyl-diamino moiety.

The syntheses of variously substituted 1,2-diamino-cyclobutene-3,4-diones are described in the following publications: Tietze et al., Chem Ber. 1991, 124, 1215; Tietze et al., Bioconjugate Chem. 1991, 2, 148; Ehrhardt et al., Chem. Ber. 1977, 110, 2506, and Neuse et al., Liebigs Ann. Chem. 1973, 619.

DESCRIPTION OF THE INVENTION

In accordance with the present invention, there is provided a group of compounds represented by the formula (I):

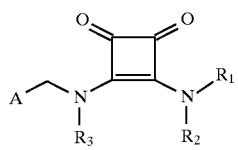

wherein:
$R_1$ and $R_2$ are, independently, hydrogen, straight chain alkyl of 1 to 10 carbon atoms, branched chain alkyl of 3 to 10 carbon atoms, cycloalkyl of 3 to 8 carbon atoms, bicycloalkyl of 4 to 10 carbon atoms or aralkyl of 7 to 20 carbon atoms, wherein the aromatic moiety of the aralkyl group may be optionally substituted with one to three straight chain alkyl of 1 to 10 carbon atoms, branched chain alkyl of 1 to 10 carbon atoms, halogen, nitro, cyano, alkoxy of 1 to 6 carbon atoms, alkoxycarbonyl of 2 to 7 carbon atoms, trifluoromethyl or trifluoromethoxy groups;

$R_3$ is hydrogen, formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

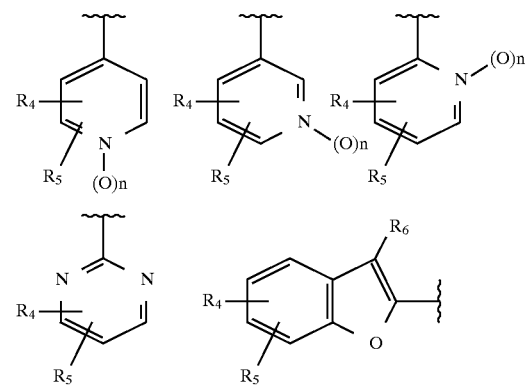

wherein:

n is 0 or 1;

$R_4$, $R_5$ and $R_6$ are, independently, cyano, nitro, amino, alkyl of 1 to 6 carbon atoms, perfluoroalkyl of 1 to 6 carbon atoms, alkoxy, of 1 to 6 carbon atoms, perfluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, alkylcarboxamido of 2 to 7 carbon atoms, arylcarboxamido of 7 to 13 carbon atoms, alkanoyl of 2 to 6 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen; or a pharmaceutically acceptable salt thereof.

A preferred aspect of this invention includes compounds of formula (I) wherein:

$R_1$ and $R_2$ are as stated above;

$R_3$ is hydrogen;

A is selected from the following:

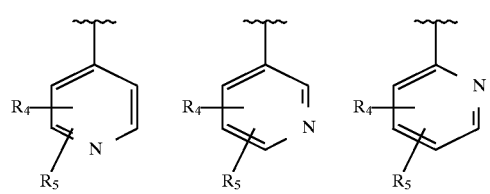

-continued

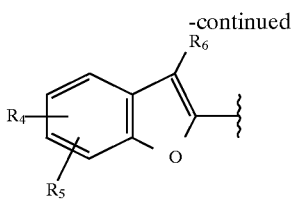

wherein:

R₄, R₅ and R₆ are as defined above;
or a pharmaceutically acceptable salt thereof.

It is understood that the definition of the compounds of formula (I), when $R_1$, $R_2$, $R_3$, $R_4$, $R_5$ or $R_6$ contain asymmetric chiral centers, encompasses all possible stereoisomers and mixtures thereof which possess the activity discussed below. In particular, it encompasses racemic modifications and any optical isomers which possess the indicated activity. Optical isomers may be obtained in pure form by standard separation techniques or enantiomer specific synthesis. It is understood that this invention encompasses all crystalline forms of compounds of formula (I). The compounds of this invention, throughout this specification, are equivalently named as 3,4-diones or 1,2-diones. The pharmaceutically acceptable salts of the basic compounds of this invention are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where $R_4$, $R_5$ or $R_6$ contains a carboxyl group, salts of the compounds of this invention may be formed with bases such as alkali metals (Na, K, Li) or the alkaline earth metals (Ca or Mg).

The present invention also provides a process for the preparation of a compound of formula (I). More particularly, the compounds of formula (I) may be prepared by reacting a compound of formula (II):

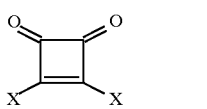
(II)

wherein X is a suitable leaving group, for example, methoxy, ethoxy, isopropoxy, butoxy, halogen or a similar leaving group with a compound of formula (III):

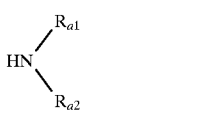
(III)

wherein $R_{a1}$ and $R_{a2}$ are $R_1$ and $R_2$, respectively, as defined hereinbefore or a group of atoms convertible thereto. The subsequent intermediate may then be allowed to react with a compound of formula (IV):

(IV)

wherein $A_1$ is A as defined hereinbefore or a group of atoms convertible thereto. The reactions mentioned above may be carried out in a solvent such as acetonitrile, methanol, ethanol, tetrahydrofuran or dioxane at elevated or ambient temperatures. Furthermore, the order of reaction may be reversed, that is, a compound of formula (II) may be allowed to react initially with a compound of formula (IV), The subsequent intermediate may then be allowed to react with a compound of formula (III) as described hereinbefore, to give the compounds of formula (I).

The compounds of formula (I) and their pharmaceutically acceptable salts are smooth muscle relaxants functioning via potassium channel activation. They are therefore useful in the treatment of disorders associated with smooth muscle contraction, disorders involving excessive smooth muscle contraction of the urinary tract (such as incontinence), or of the gastrointestinal tract (such as irritable bowel syndrome), asthma and hair loss. Furthermore, the compounds of formula (I) are, as potassium channel activators, useful for treatment of peripheral vascular disease, hypertension, congestive heart failure, stroke, anxiety, cerebral anoxia and other neurodegenerative disorders.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLE 1

3-(1,1-Dimethylpropylamino)-4-[(pyridin-4-ylmethyl)-amino]-cyclobut-3-ene-1,2-dione A solution of 3,4-dibutoxycyclobut-3-ene-1,2-dione (4.526 g, 20 mmol) and 1,1-dimethylpropylamine (1.743 g, 20 mmol) in tetrahydrofuran (20 mL) was stirred at room temperature for 19.5 hours. The solvent was removed and the residue was chromatographed (gravity, chloroform-hexane) on neutral, activity III silica (150 g). The white solid isolated from the appropriate eluates was recrystallized from hexane to give 4.105 g (86%) of a white product: mp 56.5°–57.5° C. (softens 55.5° C.), One gram of this material was recrystallized twice from hexane to provide 0.794 g of 3-butoxy-4-(1,1-dimethylpropylamino)-cyclobut-3-ene-1,2-dione as a white solid: mp 56°–57° C. (softens 55° C.); $^1$H NMR (DMSO-d$_6$): δ 8.63 and 8.48 (two br s 1H, rotomers), 4.67 (m, br, 2H), 1.67 (m, br, 4H), 1.39 (m, 2H), 1.26 (m, br, 6H), 0.91 (t, 3H), 0.78 (t, 3H). IR (KBr): 3170, 1790, 1700 cm$^{-1}$; MS (m/z) 239 (M$^+$).

A solution of the above 3-butoxy-4-(1,1-dimethylpropylamino)-cyclobut-3-ene-1,2-dione (1.197 g, 5.0 mmol) and 4-aminomethylpyridine (0.541 g) in tetrahydrofuran (10 mL) was stirred at room temperature for 23 hours. The mixture was freed of solvent and the residue was triturated with diethyl ether and dried to provide 1.154 g of a buff solid. Recrystallization (twice) of the crude product from methanol gave 0.832 g (61%) of 3-(1,1-dimethylpropylamino)-4-[(pyridin-4-ylmethyl)-amino] cyclobut-3-ene-1,2-dione as a white compound: mp 258.0°–259.5° C. dec (softens 257.5° C.); $^1$H NMR (DMSO-d$_6$): δ 8.56 (m, 2H), 7.86 (m, br, 1H), 7.46 (s, br, 1H), 7.32 (m, 2H), 4.77 (d, 2H), 1.67 (q, 2H), 1.32 (s, 6H), 0.83 (t, 3H). IR (KBr): 3270, 1790, 1650 cm$^{-1}$; MS (m/z) 273 (M$^+$).

Elemental Analysis for $C_{15}H_{19}N_3O_2$ Calcd: C, 65.91; H, 7.01; N, 15.37 Found: C, 65.55; H, 6.88; N, 15.12

EXAMPLE 2

3-(1,1-Dimethylpropylamino)-4-[pyridin-3-ylmethyl)amino]cyclobut-3-ene-1,2-dione Tetrahydrofuran (10 mL), 3-butoxy-4-(1,1-dimethylpropylamino)cyclobut-3-ene-1,2-dione (1.197 g, 5.0 mmol, as prepared in Example 1), and 3-aminomethyl-pyridine (0.541 g) were stirred together at room temperature for 24 hours. The reaction mass was freed of solvent and the residue was triturated with diethyl ether and dried to afford 1.228 g of a cream-colored solid. Two recrystallizations of this material from methanol provided 0.887 g (65%) of 3-(1,1-dimethylpropylamino)-4-[pyridin-3-ylmethyl) amino]cyclobut-3-ene-1,2-dione as a white solid: mp 263.5°–264.5° C. (softens 260.0° C.); $^1$H NMR (DMSO-d$_6$): δ 8.57 (m, 1H), 8.52 (m, 1H), 7.80 (m, br, 1H), 7.76 (m, 1H), 7.41 (m, 1H), 7.39 (s, br, 1H), 4.72 (d, 2H), 1.66 (q, 2H), 1.30 (s, 6h), 0.82 (t, 3H). IR (KBr): 3230, 1790, 1650 cm$^{-1}$; MS (m/z): 274 (M+H)$^+$.

Elemental Analysis for $C_{15}H_{14}N_3O_2$ Calcd: C, 65.91; H, 7.01; N, 15.37 Found: C, 66.23; H, 7.08; N, 15.38

EXAMPLE 3

3-(1,1-Dimethylpropylamino)-4-[(pyridin-2-ylmethyl)amino]-cyclobut-3-ene-1,2-dione A solution of 3-butoxy-4-(1,1 -dimethylpropylamino)-cyclobut-3-ene-1,2-dione (0.622 g, 2.6 mmol, as prepared in Example 1) and 2-aminomethylpyridine (0.281 g, 2.6 mmol) in tetrahydrofuran (5 mL) was stirred at room temperature for 22 hours. Removal of solvent, trituration of the residue with diethyl ether and drying gave 0.656 g white solid. Recrystallization (twice) of the crude product from acetonitrile afforded 0.447 g (63%) of 3-(1,1-dimethylpropylamino)-4-[(pyridin-2-ylmethyl)amino]-cyclobut-3-ene-1,2-dione as a white solid: mp 192.0°–192.5° C. (softens 188.5°); $^1$H NMR (DMSO-d$_6$): δ 8.58 (m, 1H), 8.00 (m, br, 1H), 7.82 (m, 1H), 7.58 (s, br, 1H), 7.37 (m, 1H), 7.33 (m, 1H), 4.85 (d, 2H), 1.67 (q, 2H), 1.31 (s, 6H), 0.83 (t, 3H). IR (KBr): 3210, 1790, 1660 cm$^{-1}$; MS (m/z): 273 (M$^+$).

Elemental Analysis for $C_{15}H_{19}N_3O_2$ Calcd: C, 65.91; H, 7.01; N, 15.37 Found: C, 65.78; H, 6.94; N, 15.48

EXAMPLE 4

3-tert-Butylamino-4-[(pyridin-4-ylmethyl)amino]-cyclobut-3-ene-1,2-dione

In a procedure similar to that described in Example 1 utilizing the appropriate starting materials, 3-tert-butylamino-4-[(pyridin-4-ylmethyl)amino]-cyclobut-3-ene-1,2-dione was prepared as a white solid: mp 271.0°–271.5° C. (softens at 269.5° C.).

EXAMPLE 5

3-tert-Butylamino-4-[(pyridin-3-ylmethyl)amino]-cyclobut-3-ene-1,2-dione

In a procedure similar to that described in Example 1 utilizing the appropriate starting materials, 3-tert-butylamino-4-[(pyridin-3-ylmethyl)amino]-cyclobut-3-ene-1,2-dione was prepared as a white solid: mp 296.0° C. dec. (softens at 290.5° C.).

EXAMPLE 6

3-tert-Butylamino-4-[(pyridin-2-ylmethyl)amino]-cyclobut-3-ene-1,2-dione

In a procedure similar to that described in Example 1 utilizing the appropriate starting materials, 3-tert-butylamino-4-[(pyridin-2-ylmethyl)amino]-cyclobut-3-ene-1,2-dione was prepared as a white solid: mp 236.0°–236.5° C. dec. (softens at 233.5° C.).

EXAMPLE 7

3-(Isopropyl-methyl-amino)-4-[(pyridin-4-ylmethyl)-amino]-cyclobut-3-ene-1,2-dione In a procedure similar to that described in Example 1 utilizing the appropriate starting materials, 3-(isopropyl-methyl-amino)-4-[(pyridin-4-ylmethyl)-amino]-cyclobut-3-ene-1,2-dione was prepared as a white solid: mp 214.5°–215.0° C. dec. (softens at 211.5° C.).

EXAMPLE 8

3-[(5-Nitro-benzofuran-2-ylmethyl)-amino-4-(1,2,2-trimethylpropylamino)-cyclobut-3-ene-1,2-dione To a suspension of NaH (3.41 g, 80%, 113.6 mmol) in dimethylformamide (400 mL) at 0° C. was added acetone oxime (7.61 g, 104.1 mmol). After stirring for 1 hour at 0° C., 4-nitrofluorobenzene (10.00 mL, 94.6 mmol) was introduced via syringe and the resulting mixture was stirred for 1 hour. Brine (400 mL) was added and the resulting precipitate was collected by filtration. The product was washed with water and dried in vacuo to afford 18 g (100%) of white solid: $^1$H NMR (DMSO-d$_6$): δ 8.20 (d, 2H), 7.25 (d, 2H), 2.06 (s 3H), 2.11 (s, 3H).

The above oxime adduct (10.39 g, 53.56 mmol) was heated in saturated ethanolic HCl (200 mL) at reflux. After 3 hours, the reaction mixture was cooled and concentrated to ¼ volume. Water was added and the precipitated cyclization product was collected by filtration to afford 9.0 g (95%) of 2-methyl-5-nitrobenzofuran: $^1$H NMR (DMSO-d$_6$): δ 8.39 (d, 1H), 8.15 (dd, 1H), 7.45 (d, 1H), 6.49 (s, 1H), 2.48 (s, 3H).

To a stirring solution of the above benzofuran (5.00 g, 28.25 mmol) and benzoyl peroxide (0.68 g, 2.83 mmol) in carbon tetrachloride (200 mL) was added 1,3-dibromo-5,5- dimethylhydantoin (4.04 g, 14.12 mmol). The mixture was irradiated with a 200 watt lamp while stirring for 1 hour, cooled and partitioned between dichloromethane/water. The organic phase was washed with water (2×100 mL) and brine (2×100 mL), dried (MgSO$_4$), decolorized (charcoal), and concentrated in vacuo to afford 7.12 g of crude product. Recrystallization from ethyl acetate/hexane afforded 4.38 g (61%) of 2-bromomethyl-5-nitro-benzofuran as an off-white solid: $^1$H NMR (CDCl$_3$): δ 8.49 (d, 1H), 8.25 (dd, 1H), 7.58 (d, 1H), 6.91 (s, 1H), 4.59 (s, 2H).

A mixture of the above 2-bromomethyl-5-nitrobenzofuran (1.57 g, 6.13 mmol), potassium phthalimide (1.70 g, 9.19 mmol), and 18-crown-6 (0.161 g, 0.61 mmol) was stirred in acetonitrile (15 mL) overnight at room temperature. The solvent was removed by vacuum, and the residue was partitioned between ethyl acetate and brine. The organic phase was washed with 0.1N sodium hydroxide (2×50 mL) then brine (2×50 mL), dried (MgSO$_4$) and concentrated to afford an off-white solid. The crude product was triturated with cold ethyl acetate/diethyl ether/hexane to afford 1.47 g (74%) of phthalimide adduct as a white solid: $^1$H NMR (DMSO-d$_6$): δ 8.55 (d, 1H), 8.17 (dd, 1H), 7.88 (m, 4H), 7.75 (d, 1H), 5.00 (s, 2H).

The above phthalimide adduct (1.45 g, 4.49 mmol) was treated with hydrazine hydrate (0.38 mL) in refluxing ethanol (15 mL) for 1.5 hours. The reaction was cooled to 0° C. and acidified (conc. HCl) to pH=1. The mixture was filtered and the solid was washed with 6N HCl and water. The filtrate was basified with potassium carbonate and then extracted with ethylacetate. The organic phase was dried (MgSO$_4$) and concentrated to afford 0.74 g (86%) of 2-aminomethyl-5-nitrobenzofuran as a light yellow solid: $^1$H NMR (DMSO-d$_6$): δ 8.55 (d, 1H), 8.11 (dd, 1H), 7.72 (d, 1H), 6.85.(s, 1H), 3.84 (s, 2H), 2.00 (brs, 2H).

To the 2-aminomethyl-5-nitrobenzofuran (0.74 g, 3.85 mmol) stirring in tetrahydrofuran (15 mL) at 0° C. was added 3,4-dibutoxy-3-cyclobutene-1,2-dione (1.25 mL, 5.78 mmol) via syringe. The mixture was stirred for 5 hours at room temperature and was then concentrated in vacuo. The residue was crystallized from ethyl acetate/diethyl ether/hexanes to afford 0.83 g of adduct as an off-white solid. A second crop (0.17 g) was isolated from the mother liquor. Total yield: 75%. $^1$H NMR (DMSO-d$_6$): δ 9.40 and 9.20 (2 br m, 1H rotameric), 8.60 (d, 1H), 8.20 (dd, 1H), 7.80 (d, 1H), 7.04 (s, 1H), 4.88 and 4.67 (2 br m, 2H, rotameric), 4.60 (t, 2H), 1.67 (m, 2H), 1.30 (m, 2H), 0.85 (m, 3H).

3-Butoxy-4-[(5-nitro-benzofuran-2-ylmethyl)-amino]-cyclobut-3-ene-1,2-dione (0.250 g, 0.727 mmol) was dissolved in an ethanolic solution of R(+)-2-amino-3,3-dimethylbutane (0.167N, 6.0 mL, 1.00 mmol). The mixture was diluted with ethanol (1 mL) and tetrahydrofuran (1 mL). After 3 hours, an additional 6.0 mL of ethanolic amine (1.00 mmol) was added and the mixture was allowed to stir for 48 hours at room temperature. The heterogeneous mixture was diluted with 1:1 diethylether/ethyl aceate and filtered to afford 0.20 g (74%) of (R) isomer of 3-[(5-nitro-benzofuran-2-ylmethyl)-amino]-4-(1,2,2-trimethylpropylamino)-cyclobut-3-ene-1,2-dione: mp>300° C.; $^1$H NMR (DMSO-d$_6$): δ 8.61 (d, 1H), 8.21 (dd, 1H), 7.88 (d and m, 2H), 7.35 (br d, 1H), 7.06 (s, 1H), 4.98 (m, 2H), 3.92 (m, 1H), 1.10 (d, 3H), 0.86 (s, 9H). IR (KBr): 3180, 2950, 1800, 1650, 1550 cm$^{-1}$; MS (m/z) 371 (M$^+$).

Elemental Analysis for C$_{19}$H$_{21}$N$_3$O$_5$ Calcd: C, 61.45; H, 5.70; N, 11.31 Found: C, 60.52; H, 5.50; N, 11.21

EXAMPLE 9

3-(1,1-Dimethyl-propylamino)-4-[(5-nitro-benzofuran-2-ylmethyl)-amino]-cyclobut-3-ene-1,2-dione To 3-butoxy-4-[(5-nitro-benzofuran-2-ylmethyl)-amino]-cyclobut-3-ene-1,2-dione (0.25 g, 0.727 mmol), as prepared in Example 8, in ethanol (5 mL) was added tert-amylamine (0.53 mL, 4.54 mmol). The reaction was stirred at 70° C. for 18 hours and then at room temperature for 48 hours. The precipitated product was filtered and washed with ethyl acetate, diethyl ether, and petroleum ether to afford 0.22 g (85%) of 3-(1,1-dimethyl-propylamino)-4-[(5-nitro-benzofuran-2-ylmethyl)-amino]-cyclobut-3-ene-1,2-dione as an off-white solid: mp 283.5°–287.5° C. (dec); $^1$H NMR (DMSO-d$_6$): δ 8.61 (d, 1H), 8.18 (dd, 1H), 7.96 (br t, 1H), 7.81 (d, 1H), 7.46 (br s, 1H), 7.07 (s, 1H), 4.99 (d, 2H), 1.66 (q, 2H), 1.30 (s, 6H), 0.82 (t, 3H). IR (KBr): 3220, 2950, 1800 cm$^{-1}$; MS (m/z) 357 (M$^+$).

Elemental Analysis for C$_{18}$H$_{19}$N$_3$O$_5$ Calcd: C, 60.50; H, 5.36; N, 11.76 Found: C, 59.31; H. 5.15; N, 11.53

EXAMPLE 10

3-tert-Butylamino-4-[(5-nitro-benzofuran-2-ylmethyl)-amino]-cyclobut-3-ene-1,2-dione To 3-butoxy-4-[(5-nitro-benzofuran-2-ylmethyl)amino]-cyclobut-3-ene-1,2-dione (0.25 g, 0.727 mmol), as prepared in Example 8, in ethanol (5 mL) was added tert-butylamine (0.51 mL, 4.85 mmol). The reaction was stirred at 70° C. for 18 hours and then at room temperature for 48 hours. Workup in a manner identical to Example 9 afforded 0.20 g (80%) of 3-tert-butylamino-4-[(5-nitro-benzofuran-2-ylmethyl)-amino]-cyclobut-3-ene-1,2-dione as an off-white solid: mp>300° C.; $^1$H NMR (DMSO-d$_6$): δ 8.61 (d, 1H), 8.20 (dd, 1H), 7.91 (br t, 1H), 7.81 (d, 1H), 7.59 (br s, 1H), 7.07 (s, 1H), 4.98 (d, 2H), 1.36 (s, 9H). IR (KBr): 3220, 2930, 1800, 1675 cm$^{-1}$; MS (m/z) 344.3 [M+H]$^+$.

Elemental Analysis for C$_{17}$H$_{17}$N$_3$O$_5$ Calcd: C, 59.47; H, 4.99; N, 12.24 Found: C, 58.86; Hm 4.78; N, 11.88

EXAMPLE 11

2-{[2-(1,1-Dimethyl-propylamino)-3,4-dioxo-cyclobut-1-enylamino]-methyl}-benzofuran-5-carbonitrile Acetone oxime (6.34 g, 86.64 mmol) was added to a suspension of sodium hydride (as a 80% dispersion in mineral oil; 2.72 g, 90.82 mmol) in N,N-dimethylformamide (400 mL) at 0° C. The frothy suspension was stirred for 1 hour as the mixture was warmed to 25° C. p-Fluorobenzonitrile (10.00 g, 82.51 mmol) was added and the reaction mixture was stirred at 0° C. for 15 minutes and then allowed to warm to room temperature. After stirring overnight, the reaction mixture was poured into brine (300 mL). The resulting white precipitate was collected by filtration, washed with water, and dried in vacuo. Yield: 13.97 g (98%): $^1$H NMR (DMSO-d$_6$): δ 7.78 (d, 2H), 7.76 (d, 2H), 2.04 (s, 3H), 2.00 (s, 3H).

To the product of the proceeding paragraph (13.97 g, 80.28 mmol) was added ethanolic hydrochloric acid (400 mL). The mixture was heated at reflux for 4 hours. The reaction mixture was cooled and concentrated to ⅓ the volume. The reaction mixture was diluted with water, resulting in the instantaneous formation of a precipitate. The precipitate was collected by filtration, washed with water, and dried in vacuo. The crude product was purified by HPLC (10:1, hexane/ethyl acetate). Yield: 7.26 g (58%): $^1$H NMR (CDCl$_3$): δ 7.79 (d, 1H), 7.47 (dd, 1H), 7.43 (d, 1H), 6.44 (s, 1H), 2.47 (s, 3H).

To a solution of the product of the proceeding paragraph (3.00 g, 19.08 mmol) in carbon tetrachloride (80 mL) was added benzoyl peroxide (0.46 g, 1.91 mmol) and 1,3- dibromo-5, 5-dimethylhydantoin (2.73 g, 9.54 mmol). The reaction mixture was irradiated with a 200 watt lamp for 1 hour. The reaction mixture was cooled and partitioned between ethyl acetate and sodium bicarbonate. The organic layer was dried over magnesium sulfate, treated with Norite® (activated carbon), filtered and concentrated to a solid. The crude product was recrystallized from ethyl acetate/hexane. Yield: 2.40 g (59%): $^1$H NMR (DMSO-d$_6$): δ 8.49 (d, 1H), 8.25 (dd, 1H), 7.58 (d, 1H), 6.91 (s, 1H), 4.59 (s, 2H).

To a solution of the product of the proceeding paragraph (2.63 g, 10.27 mmol) in acetonitrile (30 mL) was added potassium phthalimide (2.85 g, 15.41 mmol) and 18-crown-6 (0.27 g, 1.03 mmol). After stirring overnight, the reaction mixture was concentrated in vacuo. The residue was partitioned between ethyl acetate and brine and immediately a precipitate formed. The precipitate was collected by filtration, washed with diethyl ether and dried. The organic phase was washed with 0.1N sodium hydroxide (2×50 mL) and then brine (2×50 mL). The solution was concentrated in vacuo to afford another batch of solid. Yield: 2.50 g (76%): $^1$H NMR (DMSO-d$_6$): δ 8.18 (d, 1H), 7.91 (m, 4H), 7.77 (dd, 1H), 7.74 (d, 1H), 7.07 (d, 1H), 5.00 (s, 2H).

To a solution of the product of the proceeding paragraph (2.50 g, 7.74 mmol) in ethanol (20 mL) was added hydrazine-hydrate (0.66 mL). The mixture was heated to reflux for 1.5 hours. The reaction mixture was cooled to 0° C. and acidified with concentrated hydrochloric acid to pH of 1. The mixture was filtered and the filter cake was washed with 6N hydrochloric acid and then water. The filtrate was basified with potassium carbonate and extracted with ethyl acetate. The organic phase was dried over magnesium sulfate, treated with Norite®, and concentrated to afford an off white solid. Yield: 0.85 g (62%): $^1$H NMR (DMSO-d$_6$): δ 8.17 (d, 1H), 7.78 (dd, 1H), 7.74 (d, 1H), 6.82 (s, 1H), 3.85 (s, 2H), 2.10 (br s, 2H).

To a solution of the product of the proceeding paragraph (0.84 g, 4.40 mmol) in tetrahydrofuran (15 mL) was added 3,4-diethoxy-3-cyclobutene-1,2-dione (1.13 g, 6.60 mmol) at 0° C. The reaction mixture was warmed to room temperature and stirred for 4 hours. The reaction mixture was concentrated in vacuo and the crude product was triturated with ethyl acetate/diethyl ether/hexane to yield an off white solid. The solid was filtered and dried to yield the desired product. Yield: 1.05 g (76%): $^1$H NMR (DMSO-d$_6$): δ 9.41 and 9.21 (br m, 1H, rotamers), 8.22 (d, 1H), 7.81 (dd, 1H), 7.00 (s, 1H), 4.88 and 4.68 (2 br m, 2H, rotamers), 4.65 (t, 2H), 1.39 (m, 3H).

To a solution of the product of the proceeding paragraph (0.25 g, 0.79 mmol) in ethanol (17 mL) was added tert-amyl amine (0.21 g, 2.37 mmol). The reaction mixture was heated at 70° C. and allowed to stir overnight. The solid which had formed was filtered and washed with ethyl acetate, diethyl ether, and hexane to afford 0.18 g (67%) of 2-{[2-(1,1-dimethyl-propylamino)-3,4-dioxo-cyclobut-1-enylamino]-methyl}-benzofuran-5-carbonitrile as an off white solid: mp 171.1°–173.2° C.; $^1$H NMR (DMSO-d$_6$): δ 8.19 (d, 1H), 7.96 (t, 1H), 7.81 (d, 1H), 7.74 (dd, 1H), 7.45 (s, 1H), 6.96 (s, 1H), 4.97 (d, 2H), 1.67 (q, 2H), 1.29 (s, 6H), 0.83 (t, 3H). IR (KBr): 3230, 2950, 2220, 1800 cm$^{-1}$; MS (m/z) 337 (M$^+$).

Elemental analysis for $C_{19}H_{19}N_3O_3$ Calc'd: C, 67.64; H, 5.68; N, 12.46. Found: C, 66.87; H, 5.32; N, 12.37.

EXAMPLE 12

2-{[3,4-Dioxo-2-(1,2,2-trimethyl-propylamino)-cyclobut-1-enylamino]-methyl}-benzofuran-5-carbonitrile To a solution of the product of paragraph 6 in Example 11 (0.250 g, 0.79 mmol) in ethanol (2 mL) was added ethanolic (R)-2-amino-3,3-dimethylbutane (0.166N in EtOH, 9.50 mL, 1.58 mmol). The reaction mixture was heated at 70° C. and allowed to stir overnight. The solid which had formed was filtered and washed with ethyl acetate, diethyl ether, and hexane. The solid was dried in vacuo to 0.22 g (79%) of the (1R) isomer of 2-{[3,4-dioxo-2-(1,2,2-trimethyl-propylamino)-cyclobut-1-enylamino]-methyl}-benzofuran-5-carbonitrile as an off white solid: mp>300; $^1$H NMR (DMSO-d$_6$): δ 8.18 (d, 1H), 7.80 (dd, 1H), 7.74 (dd, 1H), 7.31 (br d, 1H), 6.95 (s, 1H), 4.96 (m, 2H), 3.91 (br m, 1H), 1.11 (d, 3H), 0.81 (s, 9H). IR (KBr): 3170, 2950, 2250, 1850, 1650, 1560 cm$^{-1}$; MS (m/z) 351 (M$^+$).

Elemental analysis for $C_{20}H_{21}N_3O_3$ Calc'd: C, 68.36; H, 6.02; N, 11.96. Found: C, 68.00; H, 5.83; N, 12.00.

EXAMPLE 13

2-[(2-tert-Butylamino-3,4-dioxo-cyclobut-1-enylamino)-methyl]-benzofuran-5-carbonitrile To a solution of the product of paragraph 6 in Example 11 (0.250 g, 0.79 mmol) in ethanol (17 mL) was added tert-butyl amine (0.17g, 2.37 mmol). The reaction mixture was heated at 70° C. and allowed to stir overnight. The solid which had formed was filtered and washed with ethyl acetate, diethyl ether, and hexane. The solid was dried in vacuo to yield afford 0.12 g (51%) of 2-[(2-tert-butylamino-3,4-dioxo-cyclobut-1-enylamino)-methyl]-benzofuran-5-carbonitrile as a light pink solid: mp 298.8°–300.3° C.; $^1$H NMR (DMSO-d$_6$): δ 8.18 (d, 1H), 7.96 (t, 1H), 7.81 (dd, 1H), 7.74 (dd, 1H), 7.57 (s, 1H), 6.95 (s, 1H), 4.96 (d, 2H), 1.35 (s, 9H). IR (KBr): 3300, 2950, 2210, 1800, 1660, 1525 cm$^{-1}$; MS (m/z) 323 (M$^+$).

Elemental analysis for $C_{18}H_{17}N_3O_3$ Calc'd: C, 66.86; H, 5.30; N, 13.00 Found: C, 65.64; H, 4.93; N, 12.57

EXAMPLE 14

2-{[2-(1,1-Dimethyl-2-phenyl-ethylamino)-3,4-dioxo-cyclobut-1-enylamino]-methyl}-benzofuran-5-carbonitrile To a solution of the product of paragraph 6 in Example 11 (0.23 g, 0.73 mmol) in ethanol (20 mL) was added alpha, alpha-dimethylphenethylamine (0.33 g, 2.19 mL). The reaction mixture was heated at 70° C. and allowed to stir overnight. The solid which had formed was filtered and washed with ethyl acetate, diethyl ether, and hexane. The solid was dried in vacuo to afford 0.11 g (41%) of 2-{[2-(1,1-Dimethyl-2-phenyl-ethylamino)-3,4-dioxo-cyclobut-1-enylamino]-methyl}-benzofuran-5-carbonitrile as an off white solid: mp 233.4°–235.2° C.; $^1$H NMR (DMSO-d$_6$): δ 8.20 (d, 1H), 7.89 (t, 1H), 7.81 (dd, 1H), 7.74 (dd, 1H), 7.36 (s, 1H), 7.23 (m, 3H), 7.06 (d, 2H), 6.94 (s, 1H), 4.97 (d, 2H), 2.98 (s, 2H), 1.31 (s, 6H). IR (KBr): 3300, 3000, 2200, 1800, 1660, 1590 cm$^{-1}$; MS (m/z) 399 (M$^+$).

Elemental analysis for $C_{24}H_{21}N_3O_3$ Calc'd: C, 72.17; H, 5.30; N, 10.52 Found: C, 71.28; H, 5.20, N, 10.33

EXAMPLE 5

3-[(Pyridin-4-ylmethyl)-amino]-4-(1,2,2-trimethyl-propylamino)-cyclobut-3-ene-1,2-dione In a procedure similar to that described in Example 1 utilizing the appropriate starting materials, 3-[(pyridin-4-ylmethyl)-amino]-4-(1,2,2-trimethyl-propylamino)-cyclobut-3-ene-1,2-dione was prepared as a white solid: mp 282.5°–283.0° C. dec. (softens at 271.5° C.).

EXAMPLE 16

2-{[2-(1,1-Dimethyl-propylamino)-3,4-dioxo-cyclobut-1-enylamino]-methyl}-3-chloro-benzofuran-5-carbonitrile The benzofuran adduct prepared in Example 11, paragraph 2 was used to synthesize 3-chloro-2-methylbenzofuran-5-carbonitrile (Cross, P. E.; Dickinson, R. P.; Parry, M. J.; Randall, M. *J. J. Med. Chem.*, 1986, 29, 1643–1650). Yield: 23%: $^1$H NMR (CDCl$_3$): δ 7.81 (d, 1H), 7.55 (dd, 1H), 7.47 (dd, 1H), 2.49 (s, 3H).

3-Chloro-2-bromomethyl-benzofuran-5-carbonitrile was prepared in a manner similar to 2-bromomethyl-benzofuran-5-carbonitrile synthesized in Example 11, paragraph 3. Yield: 53%: $^1$H NMR (DMSO-d$_6$): δ 8.24 (d, 1H), 7.93 (d, 2H), 4.94 (s, 2H).

The product from the proceeding paragraph was reacted with potassium pthalamide in a manner similar to Example 11, paragraph 4 to yield the pthalimide adduct. Yield: 72%: $^1$H NMR (DMSO-d$_6$): δ 8.18 (d, 1H), 7.89 (m, 6H), 5.03 (s, 2H).

3-Chloro-2-aminomethyl-benzofuran-5-carbonitrile was prepared in a manner similar to Example 11, paragraph 5. Yield:63%: $^1$H NMR (DMSO-d$_6$): δ 8.18 (d 1H), 7.81 (dd, 2H), 3.85 (s, 2H), 3.21 (br s, 2H).

The above amino compound was reacted with 3,4-dibutoxy-3-cyclobutene-1,2-dione in a manner similar to Example 11, paragraph 6. Yield: 75%: $^1$H NMR (DMSO-d$_6$): δ 9.40 and 9.18 (br m, 1H, rotamers), 8.21 (d, 1H), 7.91 (dd, 2H), 4.98 and 4.75 (2 br m, 2H, rotamers), 4.61 (t, 2H), 1.63 (m, 2H), 1.35 (m, 2H), 0.87 (m, 3H).

To a solution of the product of the proceeding paragraph (0.14 g, 0.37 mmol) in ethanol (12 mL) was addedtert-amyl amine (0.065 g, 0.74 mmol). The reaction mixture was heated at 70° C. and allowed to stir for 13 h. The solid which had formed was filtered and washed with ethyl acetate, diethyl ether, and hexane. the solid was dried in vacuo to yield a light orange solid. Yield: 0.11 g (74%): mp 257.3°–258.1° C.; $^1$H NMR (DMSO-d$_6$): δ 8.22 (d, 1H), 7.93 (t, 1H), 7.90 (d, 1H), 7.87 ,(dd, 1H), 7.40 (s, 1H), 5.05 (d, 2H), 1.66 (q, 2H), 1.29 (s, 6H), 0.80 (t, 3H). IR (KBr): 3230, 2950, 2220, 1800 cm$^{-1}$; MS (m/z) 371 (M$^+$).

Elemental analysis for C$_{19}$H$_{18}$Cl$_1$N$_3$O$_3$ Calc'd: C, 61.38; H, 4.88; N, 11.30 Found: C, 60.75 H, 4.81; N, 11.11

The smooth muscle relaxing activity of the compounds of this invention was established in accordance with standard pharmaceutically accepted test procedures with representative compounds as follows:

Sprague-Dawley rats (150–200 g) are rendered unconscious by CO$_2$ asphyxiation and then euthanized by cervical dislocation. The bladder is removed into warm (37 deg. C.) physiological salt solution (PSS) of the following composition (mM): NaCl, 118.4; KCl, 4.7; CaCl$_2$, 2.5; MgSO$_4$, 4.7; H$_2$O, 1.2; NaHCO$_3$, 24.9; KH$_2$PO$_4$, 1.2; glucose, 11.1; EDTA, 0.023; gassed with 95% O$_2$; 2/5% CO$_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 uM carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity (IC$_{50}$ concentration) and is calculated from this concentration-response curve. The maximum percentage inhibition of contractile activity evoked by a test compound is also recorded for concentrations of test compound less than or equal to 30 μM.

The results of this study are shown in Table I.

TABLE I

Inhibition of Contractions in Isolated Rat Bladder Strips

| Compound | n | IC$_{50}$ μM |
|---|---|---|
| Example 1 | 4 | 0.42 ± 0.06 |
| Example 2 | 5 | 1.25 ± 0.39 |
| Example 3 | 4 | 1.25 ± 0.34 |
| Example 4 | 6 | 3.0 ± 0.2 |
| Example 5 | 4 | 2.63 ± 0.22 |
| Example 6 | 4 | 11.45 ± 4.3 |
| Example 7 | 4 | *I = 27.3 ± 7% |
| Example 8 | 4 | **C = 8.5 ± 1.4% |
| Example 9 | 3 | *I = 22.2 ± 7.4% |
| Example 10 | 4 | *I = 11.5 ± 3.2% |
| Example 11 | 4 | 1.56 ± 0.16 |
| Example 12 | 2 | 3.75 ± 1.44 |
|  | 2 | *I = 5.5 ± 4% |
| Example 13 | 3 | *I = 19.94 ± 8.5% |
| Example 14 | 2 | *I = 31.9 ± 6.4% |
| Example 15 | 4 | 2.45 ± 0.99 |
| Example 16 | 2 | 1.3 ± 0.63 |

*Percent inhibition at 30 μM
**Percent contraction at 30 μM

In addition, we tested the ability of the compound of Example 1, as representative of the other compounds of this invention, to inhibit the hyperactivity of hypertrophied bladder (detrussor) smooth muscle in conscious female rats with hypertrophied bladders and thereby alleviate urinary incontinence according to the protocol described by Malmgrem et al., *J. Urol.* 142:1134, 1989.

Female Sprague-Dawley rats, ranging in weight from 190–210 g are used. Up to 25 animals are prepared each time. After development of bladder hypertrophy 4–8 animals are used per test.

Compounds are dissolved in PEG-200 and administered by gastric gavage or intraveneously in a volume of 5 ml/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4-0 silk is tied around the proximal urethra in the presence of a stainless steel rod (1 mm diameter) to produce a partial occlusion. The rod is then removed. The abdominal region is closed using surgical staples and each rat receives 150,000 units of bicillin C-R. The animals are allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C-R (150000 units/rat). Two days later the animals are used in cystometrical evaluations. The animals are placed in the metabolic cages and the catheter is attached (using a "T" connector) to a Statham pressure transducer (Model P23Db) and to a Harvard infusion pump. A plastic beaker attached to a force displacement transducer (Grass FTO3) is placed under the rat's cage to collect and record urine volume. Animals are allowed 15–30 minutes to rest before the saline infusion (20 ml/hr for 20 minutes) is started for the first cystometry period. Two hours after the first cystometry period, the rats are dosed with the vehicle or the test compound and one hour later a second cystometry is performed.

The following urodynamic variables are recorded:

| | |
|---|---|
| Basal bladder pressure = | the lowest bladder pressure during cystometry |
| Threshold pressure = | bladder pressure immediately prior to micturition |
| Micturition volume = | volume expelled |
| Micturition pressure = | peak pressure during voiding |
| Spontaneous activity = | mean amplitude of bladder pressure fluctuations during filling |

Presentation of results:

The mean value of each variable is calculated before and after compound administration. For each compound the changes in the variables measured are compared to the values obtained before treatment and expressed as percent inhibition. The data are also subjected to 2-way analysis of variance to determine significant ($p<0.05$) changes in the variable measured.

The results of this study are shown in Table II

TABLE II

Inhibition of Spontaneous Contractions In Vivo

| Compound | # of animals | dose mg/kg (p.o.) | % Red (F)* |
|---|---|---|---|
| Example 1 | 3 | 10 | −8 ± 4 |

*percent reduction in the total number of spontaneous contractions in the hypertrophied rat bladder model Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally, parenterally, or by aspiration to a patient in need thereof.

What is claimed is:

1. A compound of the formula:

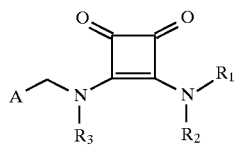

(I)

wherein:

$R_1$ and $R_2$ are, independently, hydrogen, straight chain alkyl of 1 to 10 carbon atoms, branched chain alkyl of 3 to 10 carbon atoms, cycloalkyl of 3 to 8 carbon atoms, bicycloalkyl of 4 to 10 carbon atoms or aralkyl of 7 to 20 carbon atoms, wherein the aromatic moiety of the aralkyl group may be optionally substituted with one to three straight chain alkyl of 1 to 10 carbon atoms, branched chain alkyl of 1 to 10 carbon atoms, halogen, nitro, cyano, alkoxy of 1 to 6 carbon atoms, alkoxycarbonyl of 2 to 7 carbon atoms, trifluoromethyl or trifluoromethoxy groups;

$R_3$ is hydrogen, formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

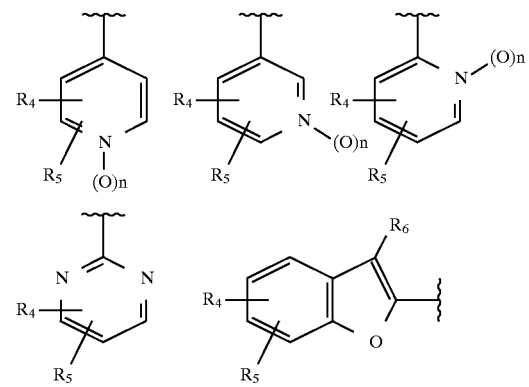

wherein:

n is 0 or 1

$R_4$, $R_5$ and $R_6$ are, independently, cyano, nitro, amino, alkyl of 1 to 6 carbon atoms, perfluoroalkyl of 1 to 6 carbon atoms, alkoxy, of 1 to 6 carbon atoms, perfluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, alkylcarboxamido of 2 to 7 carbon atoms, arylcarboxamido of 7 to 13 carbon atoms, alkanoyl of 2 to 6 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen;

or a pharmaceutically acceptable salt thereof.

2. A compound of claim 1 in which $R_3$ is hydrogen and

A is selected from the following:

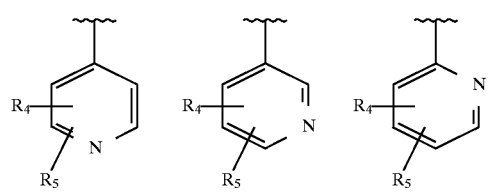

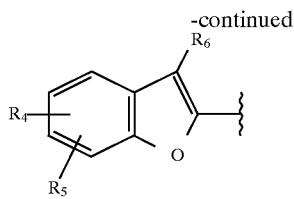

or a pharmaceutically acceptable salt thereof.

3. The compound of claim 1 which is 3-(1,1-dimethylpropylamino)-4-[(pyridin-4-ylmethyl)-amino]cyclobut-3-ene-1,2-dione or a pharmaceutically acceptable salt thereof.

4. The compound of claim 1 which is 3-(1,1-dimethylpropylamino)-4-[pyridin-3-ylmethyl)amino]cyclobut-3-ene-1,2-dione or a pharmaceutically acceptable salt thereof.

5. The compound of claim 1 which is 3-(1,1-dimethylpropylamino)-4-[(pyridin-2-ylmethyl)amino]-cyclobut-3-ene-1,2-dione or a pharmaceutically acceptable salt thereof.

6. The compound of claim 1 which is 3-tert-butylamino-4-[(pyridin-4-ylmethyl)amino]-cyclobut-3-ene-1,2-dione or a pharmaceutically acceptable salt thereof.

7. The compound of claim 1 which is 3-tert-butylamino-4-[(pyridin-3-ylmethyl)amino]-cyclobut-3-ene-1,2-dione or a pharmaceutically acceptable salt thereof.

8. The compound of claim 1 which is 3-tert-butylamino-4-[(pyridin-2-ylmethyl)amino]-cyclobut-3-ene-1,2-dione or a pharmaceutically acceptable salt thereof.

9. The compound of claim 1 which is 3-(isopropyl-methyl-amino)-4-[(pyridin-4-ylmethyl)-amino]-cyclobut-3-ene-1,2-dione or a pharmaceutically acceptable salt thereof.

10. The compound of claim 1 which is 3-[(5-nitro-benzofuran-2-ylmethyl)-amino-4-(1,2,2-trimethylpropylamino)-cyclobut-3-ene-1,2-dione or a pharmaceutically acceptable salt thereof.

11. The compound of claim 1 which is 3-(1,1-dimethylpropylamino)-4-[(5-nitro-benzofuran-2-ylmethyl)-amino]-cyclobut-3-ene-1,2-dione or a pharmaceutically acceptable salt thereof.

12. The compound of claim 1 which is 3-tert-butylamino-4-[(5-nitro-benzofuran-2-ylmethyl)-amino]-cyclobut-3-ene-1,2-dione or a pharmaceutically acceptable salt thereof.

13. The compound of claim 1 which is 2-{[2-(1,1-dimethyl-propylamino)-3,4-dioxo-cyclobut-1-enylamino]-methyl}-benzofuran-5-carbonitrile or a pharmaceutically acceptable salt thereof.

14. The compound of claim 1 which is 2-{[3,4-dioxo-2-(1,2,2-trimethylpropyamino)-cyclobut-1-enylamino]-methyl}-benzofuran-5-carbonitrile or a pharmaceutically acceptable salt thereof.

15. The compound of claim 1 which is 2-[(2-tert-butylamino-3,4-dioxo-cyclobut-1-enylamino)-methyl]-benzofuran-5-carbonitrile or a pharmaceutically acceptable salt thereof.

16. The compound of claim 1 which is 2-{[2-(1,1-dimethyl-2-phenylethyl-amino)-3,4-dioxo-cyclobut-1-enylamino]-methyl}-benzofuran-5-carbonitrile or a pharmaceutically acceptable salt thereof.

17. The compound of claim 1 which is 3-[(pyridin-4-ylmethyl)-amino]-4-(1,2,2-trimethyl-propylamino)-cyclobut-3-ene-1,2-dione or a pharmaceutically acceptable salt thereof.

18. The compound of claim 1 which is 2-{[2-(1,1-Dimethyl-propylamino)-3,4-dioxo-cyclobut-1-enylamino]-methyl}-3-chloro-benzofuran-5-carbonitrile or a pharmaceutically acceptable salt thereof.

19. A pharmaceutical composition of matter comprising a compound of the formula:

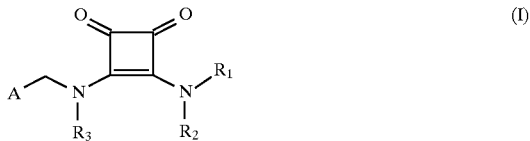

wherein:

$R_1$ and $R_2$ are, independently, hydrogen, straight chain alkyl of 1 to 10 carbon atoms, branched chain alkyl of 3 to 10 carbon atoms, cycloalkyl of 3 to 8 carbon atoms, bicycloalkyl of 4 to 10 carbon atoms or aralkyl of 7 to 20 carbon atoms, wherein the aromatic moiety of the aralkyl group may be optionally substituted with one to three straight chain alkyl of 1 to 10 carbon atoms, branched chain alkyl of 1 to 10 carbon atoms, halogen, nitro, cyano, alkoxy of 1 to 6 carbon atoms, alkoxycarbonyl of 2 to 7 carbon atoms, trifluoromethyl or trifluoromethoxy groups;

$R_3$ is hydrogen, formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

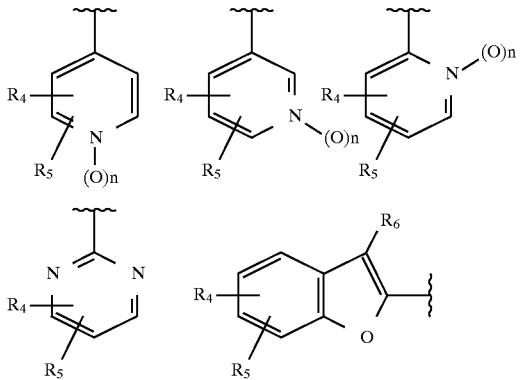

wherein:

n is 0 or 1

$R_4$, $R_5$ and $R_6$ are, independently, cyano, nitro, amino, alkyl of 1 to 6 carbon atoms, perfluoroalkyl of 1 to 6 carbon atoms, alkoxy, of 1 to 6 carbon atoms, perfluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, alkylcarboxamido of 2 to 7 carbon atoms, arylcarboxamido of 7 to 13 carbon atoms, alkanoyl of 2 to 6 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen;

or a pharmaceutically acceptable salt thereof and a pharmaceutically acceptable carrier therefor.

20. A method for reducing the adverse effects of smooth muscle contractions which comprises administering, orally or parenterally, to a patient in need thereof, a compound of the formula:

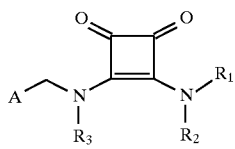

wherein:

R₁ and R₂ are, independently, hydrogen, straight chain alkyl of 1 to 10 carbon atoms, branched chain alkyl of 3 to 10 carbon atoms, cycloalkyl of 3 to 8 carbon atoms, bicycloalkyl of 4 to 10 carbon atoms or aralkyl of 7 to 20 carbon atoms, wherein the aromatic moiety of the aralkyl group may be optionally substituted with one to three straight chain alkyl of 1 to 10 carbon atoms, branched chain alkyl of 1 to 10 carbon atoms, halogen, nitro, cyano, alkoxy of 1 to 6 carbon atoms, alkoxycarbonyl of 2 to 7 carbon atoms, trifluoromethyl or trifluoromethoxy groups;

R₃ is hydrogen, formyl, alkanoyl of 2 to 7 carbon atoms, alkenoyl of 3 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

A is selected from the group consisting of:

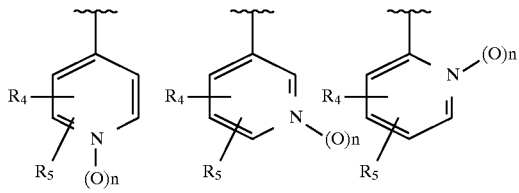

-continued

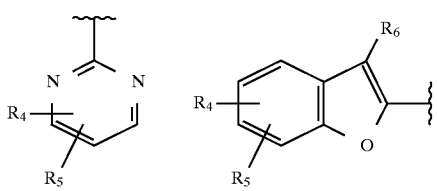

wherein:

n is 0 or 1

R₄, R₅ and R₆ are, independently, cyano, nitro, amino, alkyl of 1 to 6 carbon atoms, perfluoroalkyl of 1 to 6 carbon atoms, alkoxy, of 1 to 6 carbon atoms, perfluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, alkylcarboxamido of 2 to 7 carbon atoms, arylcarboxamido of 7 to 13 carbon atoms, alkanoyl of 2 to 6 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen;

or a pharmaceutically acceptable salt thereof.

21. The method of claim 19 in which the smooth muscle adversely contracting causes urinary incontinence.

22. The method of claim 19 in which the smooth muscle adversely contracting causes irritable bowel syndrome.

* * * * *